United States Patent [19]
Coles

[11] Patent Number: 5,314,829
[45] Date of Patent: May 24, 1994

[54] METHOD FOR IMAGING INFORMATIONAL BIOLOGICAL MOLECULES ON A SEMICONDUCTOR SUBSTRATE

[75] Inventor: L. Stephen Coles, Marina Del Rey, Calif.

[73] Assignee: California Institute of Technology, Pasadena, Calif.

[21] Appl. No.: 992,601

[22] Filed: Dec. 18, 1992

[51] Int. Cl.$^5$ .......................................... G01N 21/03
[52] U.S. Cl. ...................... 436/165; 436/56; 436/94; 436/164; 422/58; 422/82.05; 422/102; 422/104; 435/6; 250/306; 250/307; 250/311; 250/440.11; 356/244; 935/77
[58] Field of Search ............ 436/56, 63, 89, 94, 436/164, 165, 527, 422; 422/55, 58, 82.05, 104, 88, 92, 102; 250/306, 307, 311, 440.11; 435/6, 91; 204/129.3; 935/77

[56] References Cited

U.S. PATENT DOCUMENTS

| | | | |
|---|---|---|---|
| Re. 33,581 | 4/1991 | Nicoli et al. ................... | 356/337 X |
| 3,947,121 | 3/1976 | Cotter et al. ................... | 356/244 X |
| 4,729,949 | 3/1988 | Weinreb et al. ................ | 422/101 X |
| 4,808,549 | 2/1989 | Mikkor et al. ................. | 204/129.3 X |
| 4,868,396 | 9/1989 | Lindsay ......................... | 250/440.11 |
| 4,965,635 | 10/1990 | Rushefsky ....................... | 355/218 |
| 5,030,986 | 7/1991 | Dwyer, III ..................... | 355/20 |
| 5,044,001 | 8/1991 | Wang ............................. | 378/43 |
| 5,047,633 | 9/1991 | Finlan et al. .................. | 250/306 |
| 5,089,387 | 2/1992 | Tsay et al. .................... | 435/6 |
| 5,106,729 | 4/1992 | Lindsay et al. ................ | 435/810 X |
| 5,155,361 | 10/1992 | Lindsay et al. ................ | 250/440.11 X |

OTHER PUBLICATIONS

Lindsay et al. "Images of the DNA Double Helix in Water"-Science, vol. 24, Jun. 2, 1989, pp. 1063-1064.
Watson, et al., *Recombinant DNA: A Short Course*, W. H. Freeman and Cinoabtl New York, 1983, appendix A, pp. 248-253.
Ayesha Sitlani, "Sequence Specific Recognition and Photocleavage of DNA by Phenanthrenequinone Diimine Complexes or Rhodium (III)" PHD Thesis, California Institute of Technology, 1992.
David M. Glover, Gene Cloning: The Mechanics of DNA Nabuoykatuibm Chapman and Hall New York, 1984, Chapter 6 pp. 128-157.

*Primary Examiner*—Lyle A. Alexander
*Assistant Examiner*—Maureen M. Wallenhorst
*Attorney, Agent, or Firm*—Robert M. Wallace; Michael L. Keller

[57] ABSTRACT

Imaging biological molecules such as DNA at rates several times faster than conventional imaging techniques is carried out using a patterned silicon wafer having nano-machined grooves which hold individual molecular strands and periodically spaced unique bar codes permitting repeatably locating all images. The strands are coaxed into the grooves preferably using gravity and pulsed electric fields which induce electric charge attraction to the molecular strands in the bottom surfaces of the grooves. Differential imaging removes substrate artifacts.

13 Claims, 2 Drawing Sheets

METHOD FOR IMAGING INFORMATIONAL BIOLOGICAL MOLECULES ON A SEMICONDUCTOR SUBSTRATE

BACKGROUND OF THE INVENTION

Origin of the Invention

The invention described herein was made in the performance of work under a NASA contract, and is subject to the provisions of Public Law 96-517 (35 USC 202) in which the Contractor has elected to retain title.

Technical Field

The invention relates to sequencing of biological informational molecules at atomic resolution such as DNA and in particular to apparatus for holding individual DNA strands stationary and straight at known locations.

Background Art

Biologically interesting images tend to be lucky accidents and are not routinely repeatable. This occurs because the state of the art scanning tunneling electron microscope (STM) and the atomic force microscope (AFM) do not have the capacity to pan over an image in real-time. On a uniform crystal lattice, such capabilities are not required, but for non-homogeneous biological molecules, alignment of the image is essential.

Atomic resolution is achievable down to a few angstroms using either STM of AFM. However, the imaging of non-homogeneous (informational) biological molecules using these techniques has been disappointing thus far, for at least two reasons: (1) The non-reproducability of the images, preventing one from doing before and after studies to prove the absence of substrate artifacts in a fuzzy image and (2) the inability to lay the molecule down flat on a plate and have it stick rigidly to the surface for reproducible scans in different directions to enhance the signal-to-noise ratio, much as CAT Scans improve images of target tissues over a single X-Ray.

With respect to the first problem, a good metaphor to appreciate the problem is to imagine a parachutist regularly bailing out at night at 10,000 feet and trying to hit the same ground spot on successive dives. It just can't be done. The reason physicists are successful with STM or AFM imaging of crystals is that it normally doesn't matter "where you happen to touch down." For example, in the case of a metallurgist imaging the crystal lattice of an alloy, the surface is uniformly isotropic, essentially infinitely, in all directions (N, E, S, W). It doesn't matter where you look, you always see the same thing. Furthermore, there are no simple landmarks to allow one to pan over an image in real time with "x-y" micrometers and find a reproducible location, as is now routinely done in light microscopy by histologists examining specially stained pathology slides. Biologically interesting STM images published in text books tend to be lucky accidents and are not routinely repeatable.

With respect to the second problem, when DNA is stretched out in its non-coiled primary structure (double-stranded helix), it is a long fragile ungainly molecule. In its native form in the nucleus of a cell, it is normally hypercoiled in association with disklike proteins (histones) and further folded into metaloops that ultimately appear in human cells as 23 pairs of chromosomes, which during the metaphase of mitosis (cell division) assemble in a delicate structure called the spindle apparatus. In its denatured form, however, DNA and RNA tends to lie on a flat surface in a random configuration like "a plate of spaghetti," making it exceedingly difficult to image, let alone sequence.

Finally, even after one obtains a reasonable image with appropriately distributed unique markers (such as heavy metal atoms or unusual easy-to-visualize side chains) to discriminate the four basic alphabetic letters or nucleotide bases (A, G, T, C), a third problem is to "read-off" the sequence automatically.

Specimen preparation is one of the most delicate aspects of all automatic DNA sequencing technologies. Native double stranded helical DNA consists of two strands of bases paired together along the rungs of a twisted step-ladder structure. One strand is called the primary strand (for transcription of the messenger RNA), while the other strand is called the secondary strand. Although the thickness of such a double helix is only about 20 angstroms, if fully stretched out, a typical molecule could literally extend for miles. Of course, native DNA is spooled around basic protein molecules or histones, the spools being super coiled into chromosomes, referred to hereinabove, whose dimensions are in the submicron range. The information content of this long biological molecule is contained in the base-pair sequence, like the bits encoded along the length of a strip of magnetic computer tape wrapped around a spool. This is the data which is to be read. In order to do so, the DNA primary and secondary strand pair are preferably separated using well-known techniques.

SUMMARY OF THE INVENTION

Grooves etched in a semiconductor surface are used to hold biological molecules such as individual DNA strands at known reproducible locations. A grid of grooves is etched into the surface of a silicon substrate. The coordinates of each intersection of grooves in the grid is marked with, for example, a computer-readable bar code etched into the substrate surface adjacent to the intersection. A section of the grid is then imaged with an STM or AFM before a DNA specimen is placed thereon and recorded as a "before" image. Denatured DNA is then placed on the substrate and individual DNA strands are coaxed into individual grooves. Coaxing the individual DNA strands into individual grooves may entail, for example, applying an electric field across the substrate to align the strands parallel to one set of grooves and then applying an electric field through the substrate to draw the strands downwardly into the grooves. In some cases, gravity may be sufficient to coax a number of DNA strands into individual grooves. The section of the grid is again imaged to record an "after" image of both the substrate and a DNA specimen. The "before" image is then digitally subtracted from the "after" image to produce a final image of the DNA specimen alone. Confirmation that the correct "before" and "after" images are subtracted is provided by the bar codes etched near each intersection in the grid. Furthermore, the bar codes permit the STM or AFM to scan across the substrate and then return to the originally imaged section of the grid for a repeat image, whenever desired.

DETAILED DESCRIPTION OF THE INVENTION

Figure 1:
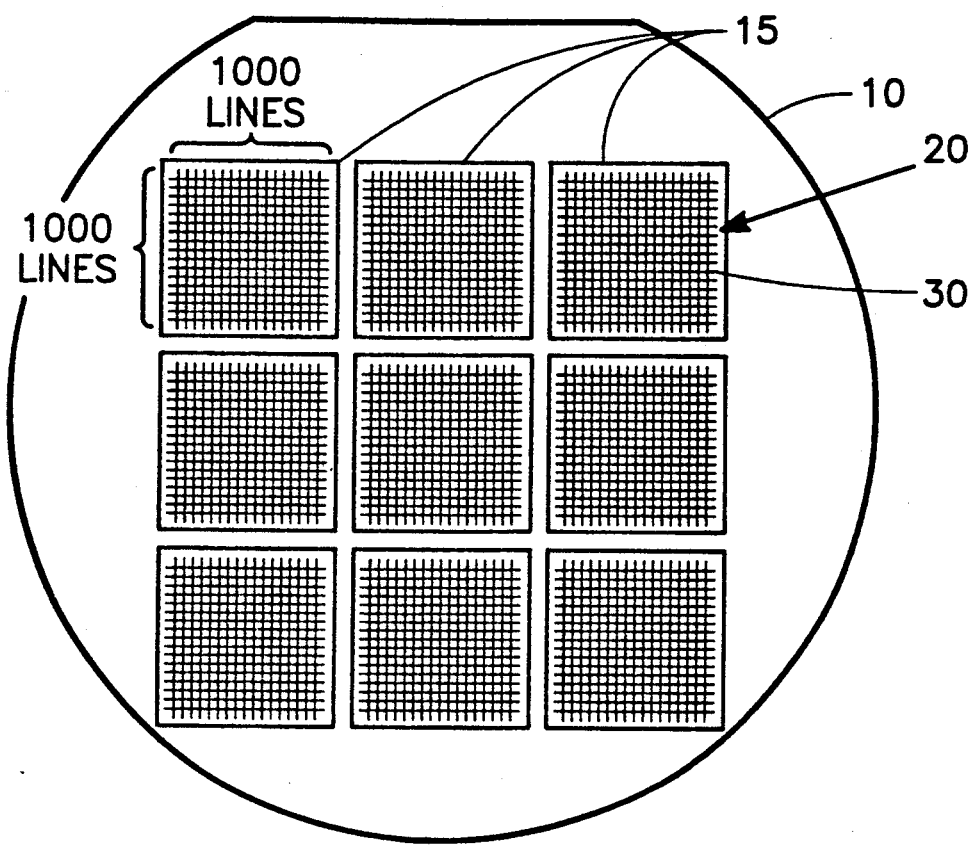
FIG. 1 is a plan view of a semiconductor wafer including diceable chips with a grid of grooves for holding DNA strands.
Figure 2:
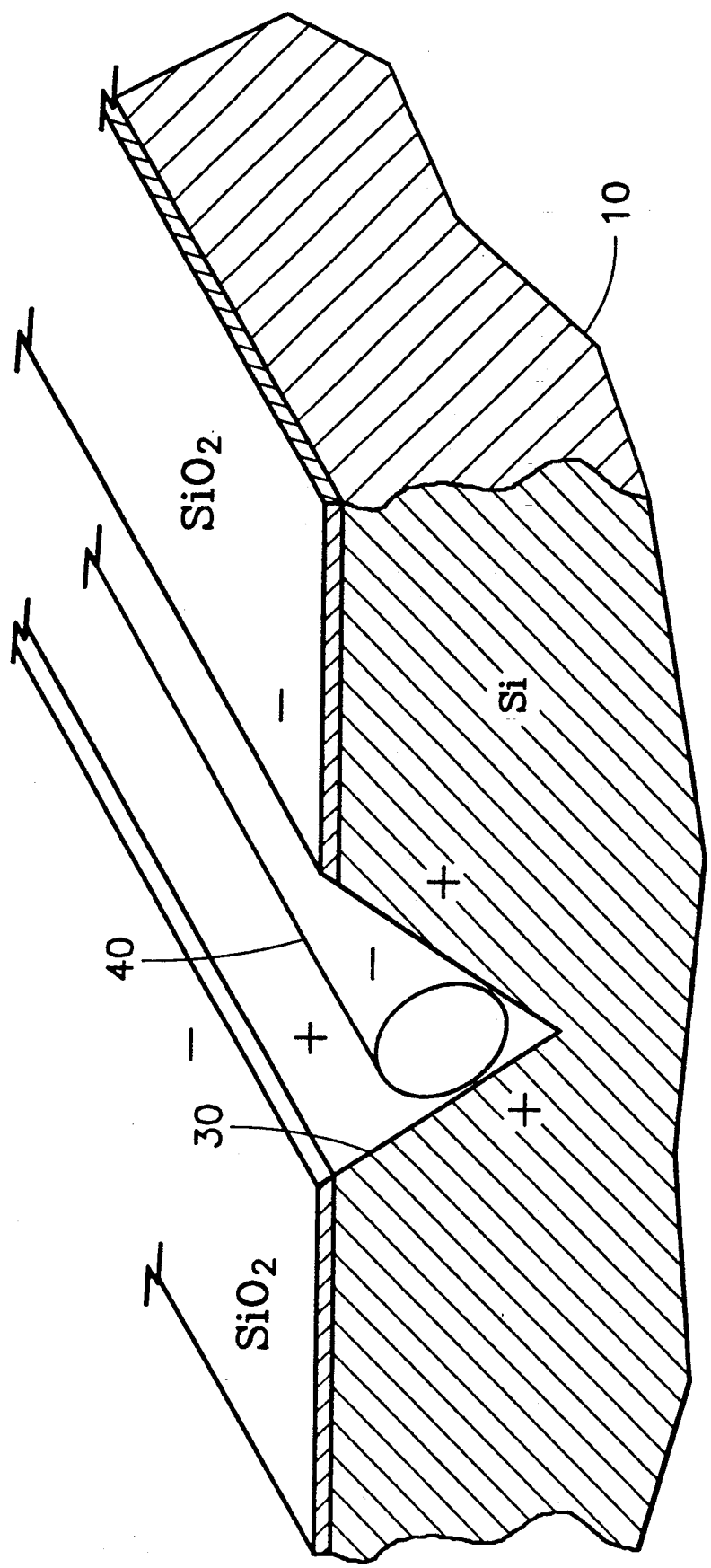
FIG. 2 is an enlarged perspective cross-sectional view of a portion of the semiconductor wafer of FIG. 1 showing one DNA strand lying in a groove.

Referring to FIG. 1, a standard 3-inch silicon wafer 10 of crystal orientation (1,0,0) has many 1-cm square dies 15 separated by 1 mm borders. Each die 15 has etched into it an orthogonal grid 20 of grooves, a typical groove 30 thereof being illustrated in the enlarged view of FIG. 2. Each 1-cm square die has 1000 grooves 30 or lines running in each orthogonal direction so that there are 1000×1000 intersections, the distance between groove centers being one micron, thus forming a 1 mm square grid within the die 15. The grid is shown proportionally oversized within the die 15 in FIG. 1 for clarity purposes. As indicated in FIG. 2, each groove is V-shaped, being about 50 nanometers in width at the top, the two sides thereof descending downwardly toward the apex at opposing 57 degree angles with respect to the vertical. This angle is the result of the reactive ion etching process employed and the substrate material.

Figure 3:
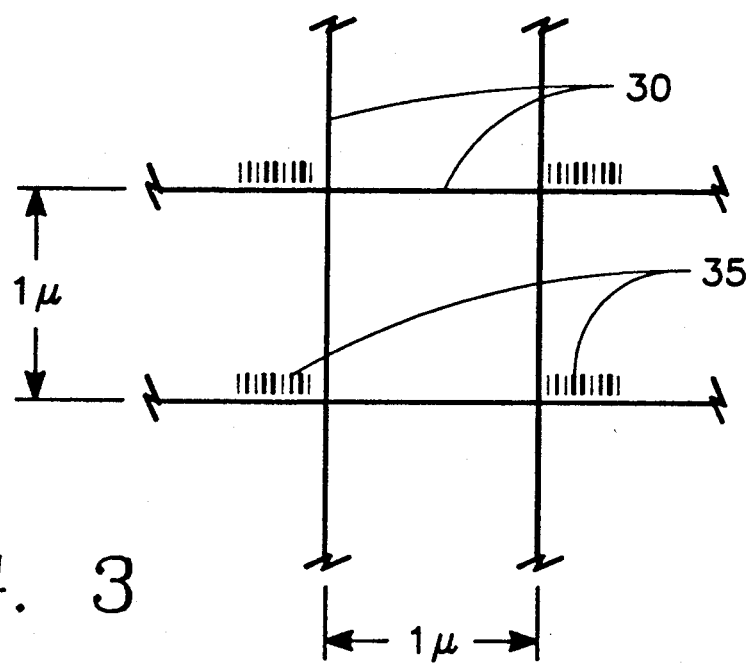
FIG. 3 is an enlarged plan view of a portion of the semiconductor wafer of FIG. 1 illustrating the bar codes at each intersection of the grid.

FIG. 3 illustrates the labelling of each intersection of orthogonal grooves 30 using a computer-readable bar code 35 photolithographically etched into the substrate surface adjacent to the intersection of a pair of orthogonal grooves 30.

The wafer 10 and die 15 of FIGS. 1-3 are fabricated as follows. Silicon wafers are cleaved in a vacuum from an extruded silicon crystal rod, and their top surfaces are highly polished to atomic smoothness (or about 5 angstroms, corresponding to the instrinsic "bumpiness of the silicon atoms). Then, a thin layer of silicon dioxide is formed on the top surface of each wafer. An electron beam direct "write step" is employed to define the grid 20 of orthogonal grooves 30 in each die 15 in a conventional reactive ion etching step. After application of the electron beam, each wafer is anisotropically etched in a bath of potassium hydroxide or ethylene diamine pyrocatechol to form the 50 nanometer grooves 30 of FIG. 2 in a conventional "nano-machining" step.

The computer-readable bar codes 35 are photolithographically etched into the top surface of the substrate using conventional photoresist and etching techniques.

Each wafer is then diced along the die borders separating the individual die 15.

A DNA specimen is prepared for depositing on the die 15 as follows. The initial step of DNA specimen preparation is to cleave the DNA into one micron fragments (containing between one thousand and two thousand DNA bases) using conventional techniques such as either ultrasound or with an appropriate restriction endonuclease, one of about 50 well-known enzymes that cuts DNA at precise locations. (See Watson et al., *Recombinant DNA: A Short Course*, W. H. Freeman and Company, New York, 1983, Appendix A, pages 348-353.) The DNA is then denatured into its single stranded form using the conventional techniques discussed earlier herein. Then, using established techniques such as the one described in Ayesha Sitlani, "Design of Rhodium Complexes to Probe Site-Specific Recognition of DNA," Ph.D Thesis, California Institute of Technology, 1992, particular heavy-metal atoms are affixed to particular bases of the DNA strand as marker-identifiers. This completes the specimen preparation process.

An eyedropper is employed to place a small drop of the prepared DNA specimen onto the top surface of the die 15. Individual DNA strands are coaxed into individual grooves 30 using a variety of techniques. Specifically, gravitational forces will help the DNA strands to drop into the grooves 30. Also, a pair of external capacitor plates may be placed along opposing sides of the die 15 and a pulsed voltage applied thereto to help aligning the DNA strands on the substrate surface in one of the two orthogonal directions of the grid of grooves 30. Finally, the DNA strands are pulled into the grooves 30 by applying an appropriate electrical field (using external capacitor plates) across the thickness of the die 15 so that the bottom surfaces of the V-shaped grooves acquire a positive charge as indicated in FIG. 2. The DNA strands have a native negative charge, and are therefore attracted by the positive charge on the bottom groove surfaces as illustrated in FIG. 2. The result is that a DNA strand 40 is pulled into a groove 30 as illustrated in FIG. 2.

The DNA strand 40 is imaged while in the groove 30 as follows. An Atomic Force Microscope (AFM) is used in accordance with the following assumptions: (1) Real time data analysis is to be performed; (2) There is a 0.5 angstrom raster line separation; (3) a 100 angstrom image width is sufficient; (4) the ATM scanning movement is parallel to the direction of the groove 30; and (5) successive bases in the DNA strand 40 are separated by 6 angstroms. The latter assumption is supported by David M. Glover, *Gene Clonino: The Mechanics of DNA Manipulation* (Chapman and Hall, New York 1986).

Before a DNA specimen is deposited onto the substrate surface of the die 15, the surface (or at least a small selected section thereof) is imaged without any DNA specimen, to record a "before" image of the substrate surface only. After the DNA specimen has been deposited onto the substrate surface, individual strands thereof are coaxed into the grooves 30. This coaxing is accomplished in several ways. First, the substrate surface is maintained in a face-up position so that gravity assists in drawing the DNA strands in to the grooves. Secondly, the DNA strands may be aligned parallel to one of the two orthogonal groove directions by applying an electric field across the substrate surface in the appropriate direction, by means of external capacitor plates temporarily held at opposing edges of the die 15. A pulsed voltage is applied across the capacitor plates. Finally, in order to pull the DNA strands into the grooves, a voltage on the order of micro-volts is applied through the thickness of the substrate (i.e., from the top surface to the bottom surface) so that the bottom surfaces of the grooves acquire a positive charge, as indicated in FIG. 2. This voltage is applied, for example, by placing external capacitor plates near the top and bottom substrate surfaces and applying a pulsed voltage across the capacitor plates to induce a voltage difference between the top and bottom of each groove 30 on the order of several microvolts.

After a sufficient coaxing of the DNA strands into the grooves in the substrate surface, the same selected area of the substrate surface is imaged to record an "after" image of a DNA strand in a groove. The "before and "after images are digitally subtracted from one another pixel-by-pixel using conventional digital image processing techniques to produce a final image of a DNA strand by itself, free of any substrate artifacts.

Before images of many sections of the grid 15 may be obtained in case it is not known which one of the sections will have an interesting DNA specimen aligned in a groove. The grid may be searched by the AFM or STM throughout those sections of the grid for which a "before" image was obtained prior to deposition of the DNA specimen. Each section of the grid 15 being unambiguously defined by the computer-readable bar codes it contains, each "after" image is readily associated with the exact "before" image for precise digital subtraction and removal of substrate artifacts in a "final" image of the DNA strand alone.

In performing the image analysis of the "final" image of the DNA strand alone, a conventional pattern recognition algorithm may be employed to automatically identify the different-sized heavy-metal atoms affixed as markers on the different DNA bases. This is but one example of an application of the present invention. In other applications, molecules other than DNA may be imaged. The main advantage of the invention is the repeatability of any image of a particular specimen by using the bar codes to re-locate previously imaged sections of the grid.

The sequencing rate (the rate at which individual DNA bases are identified along the strand) is determined by the raster length and the scan rate (linear speed of the AFM tip), as follows:

(6.0 angstroms/base/0.05 angstroms/line)×100 angstroms/line=1200 angstroms/base.

If we assume a tip speed or raster rate of 100 angstroms/sec in high-resolution imaging mode, we can obtain a sequencing rate of 6 bases per minute. As a frame of reference, the theoretical limit of Fluorescence Sequencing, such as the commercially-available machines from Applied Biosystems, Inc. of Foster City, Calif., is about 10 bases per minute. On the other hand, if we increase the tip speed of the AFM to 35,000 angstroms/sec, which is the highest rate demonstrated for "topographic mode" atomic resolution imaging, the sequencing rate of the invention is 1800 bases/minute. A further increase is obtained by increasing the tip speed to the highest rate demonstrated for "current imaging mode" atomic resolution, which is a tip speed of 100 microns/sec. This corresponds to a sequencing rate of 60,000 bases/minute. Thus, the invention offers a revolutionary improvement over the current state of the art.

While the invention has been described in detail by specific reference to preferred embodiments, it is understood that variations and modifications thereof may be made without departing from the true spirit and scope of the invention.

What is claimed is:

1. A method of imaging molecular strands using a substrate having a plurality of straight grooves in a top surface of said substrate, each of said grooves being of a size capable of holding only a single individual one of said molecular strands along any one section of a length of the groove, and being capable of forcing single individual molecular strands into a straight position when positioned in one of said plurality of grooves, said method comprising:

preparing a specimen of said molecular strands and depositing said specimen onto said top surface;

aligning and depositing individual ones of said molecular strands into individual ones of said plurality of grooves whereby the shape and size of each groove forces the molecular strands into a straight position; and recording a first image of a selected section of said top surface of said substrate having at least one of said molecular strands in one of said grooves using an atomic imaging device.

2. The method of claim 1 wherein:

said aligning and depositing of said specimen onto said top surface of said substrate is preceded by recording a preliminary image of said selected section of said substrate in the absence of any molecular strand specimen thereon using said atomic imaging device; and said recording of said first image is followed by substrating said preliminary image from said first image to produce a second image of a molecular strand by itself substantially free of image artifacts of said substrate.

3. The method of claim 2 wherein said aligning and depositing individual ones of said molecular strands into individual ones of said plurality of grooves comprises using gravity to draw said individual ones of said molecular strands into individual ones of said plurality of grooves.

4. The method of claim 2 wherein said molecular strands are of the type which are attracted by one of a positive electrical field, and a negative electrical field and wherein said aligning and depositing individual ones of said molecular strands into individual ones of said plurality of grooves comprises placing an electric field of a type which attracts said molecular strands perpendicular to said top surface of said substrate so as to draw said individual ones of said molecular strands into individual ones of said plurality of grooves.

5. The method of claim 4 wherein:

said substrate comprises a crystalline semiconductor.

6. The method of claim 4 wherein said placing an electric field perpendicular to said top surface is preceded by aligning said molecular strands in a direction parallel to at least some of said grooves.

7. The method of claim 6 wherein said aligning of said molecular strands parallel to at least some of said grooves comprises placing an electric field across said top surface of said substrate in a direction parallel to at least some of said grooves.

8. The method of claim 7 wherein said electric field parallel to at least some of said grooves is a pulsed electric field.

9. The method of claim 6 wherein said electric field perpendicular to said top surface is a pulsed electric field.

10. The method of claim 1 wherein said preparing said specimen comprises preparing a specimen of denatured DNA molecular strands.

11. The method of claim 10 wherein said preparing includes marking each of the different bases of said DNA molecular strands with a particular and unique heavy metal atom.

12. The method of claim 1 wherein said substrate further comprises address markers located at periodic locations associated with said plurality of grooves across said top surface of said substrate and wherein a different address marker uniquely identifies each of said periodic locations in said top surface of said substrate, and wherein said method of recording a first image includes recording an image of said address markers associated with said periodic locations within said selected section, whereby the location and orientation of each recorded image of a molecular strand is deducible from the address markers visible in said first image.

13. The method of claim 12 wherein each of said address markers comprises a different computer-readable bar code.

* * * * *